(12) United States Patent
Abell et al.

(10) Patent No.: US 10,363,068 B2
(45) Date of Patent: Jul. 30, 2019

(54) INSTRUMENT FOR PERCUTANEOUSLY DELIVERING A PERCUTANEOUS REVISION IMPLANT

(71) Applicant: Warsaw Orthopedic, Inc, Warsaw, IN (US)

(72) Inventors: Jeanine Abell, Memphis, TN (US); Richard Q. Brown, Collierville, TN (US); Daniel Paxton Wall, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 15/171,826

(22) Filed: Jun. 2, 2016

(65) Prior Publication Data
US 2018/0036037 A1 Feb. 8, 2018

(51) Int. Cl.
*A61B 17/70* (2006.01)
*A61B 17/02* (2006.01)
*A61B 17/88* (2006.01)

(52) U.S. Cl.
CPC ...... *A61B 17/7011* (2013.01); *A61B 17/0218* (2013.01); *A61B 17/705* (2013.01); *A61B 17/708* (2013.01); *A61B 17/7037* (2013.01); *A61B 17/7083* (2013.01); *A61B 17/7091* (2013.01); *A61B 17/7032* (2013.01); *A61B 17/88* (2013.01)

(58) Field of Classification Search
CPC .................................. A61B 17/7074–7091
USPC .......................................................... 606/86 A
See application file for complete search history.

(56) References Cited

U.S. PATENT DOCUMENTS

| | | | |
|---|---|---|---|
| 5,910,141 A * | 6/1999 | Morrison | A61B 17/7091 606/101 |
| 8,021,399 B2 | 9/2011 | Ritland | |
| 2010/0256683 A1 | 10/2010 | Ilott et al. | |
| 2011/0087287 A1 | 4/2011 | Reeder, Jr. et al. | |
| 2013/0150887 A1 | 6/2013 | McLean et al. | |
| 2015/0066089 A1* | 3/2015 | Nelson | A61B 17/7083 606/265 |
| 2016/0346017 A1* | 12/2016 | Meyer | A61B 17/8863 |

* cited by examiner

*Primary Examiner* — Nicholas J Plionis
(74) *Attorney, Agent, or Firm* — Thomas S. Wolfe

(57) ABSTRACT

The invention provides improved instruments and related methods for percutaneously delivering a revision implant to a surgical site in a spine of a patient having an existing implant installed therein. In one aspect, a percutaneous delivery instrument is provided with an inner shaft with a threaded portion at its distal end to engage a percutaneous revision implant, an outer sleeve with a hollow cavity, hinges, and features to engage the percutaneous revision implant at its distal end, and a translator in which the outer sleeve is disposed. The percutaneous delivery instrument may be employed to deliver and install a percutaneous revision implant to extend the existing implant such that it spans additional portions of the spine.

20 Claims, 13 Drawing Sheets

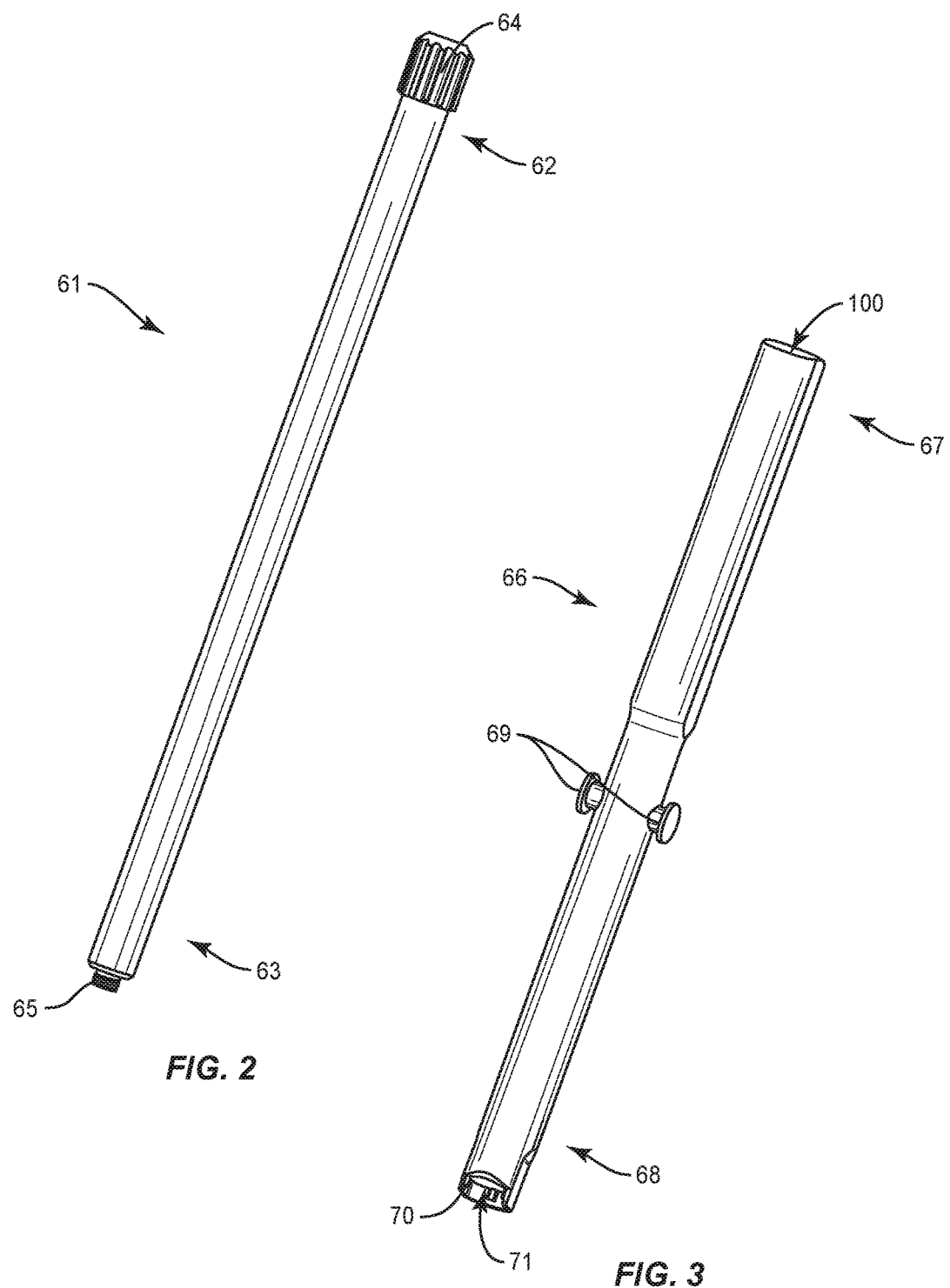

INSTRUMENT FOR PERCUTANEOUSLY DELIVERING A PERCUTANEOUS REVISION IMPLANT

FIELD OF INVENTION

The present invention generally relates to the field of implant delivery instruments, and more particularly, to an instrument for introducing and installing a percutaneous revision implant through a percutaneous access site and into a surgical site in a spinal region of a patient having an existing implant installed therein, in order to revise the existing implant, without significantly disrupting or removing components of the existing implant, and methods of using same.

BACKGROUND

Spinal implants are typically implanted when the spine of a patient is dysfunctional (e.g., misaligned or degenerated). Following surgery and/or during or after the healing process, muscular and skeletal alignment or adjustment may occur. Such alignments and adjustments may affect the patient's range of motion, the effectiveness, life expectancy, or performance of the existing spinal implant, and/or potentially cause deterioration of surrounding bones, discs, vertebrae, hips, knees, etc., or the existing implant. For example, when the abdominal and back muscles strengthen after an implant procedure, the spine may subsequently align or realign, causing the implant or its articulation faces to be impinged as a result of the alignment or realignment. Thus at times there is a need for spinal surgeons to revise (e.g., extend) an existing spinal implant installed in a patient during a prior surgical procedure. For example, a revision surgery may entail lengthening an existing implant so that it spans additional portions of the spine.

Revision-type surgeries have been developed, but difficulties with typical instrumentation and procedures remain. Ideal locations to anchor a revision implant may already be occupied by the existing implant, thereby requiring the medical practitioner to adjust, reposition, remove, or otherwise significantly disrupt the existing implant in order to insert the revision implant. Surgeons may also need to open up the region of the existing implant to obtain a better view of the surgical site. Such procedures are often performed subcutaneously (i.e., under the skin), and are highly invasive and require large incisions, such as in tissue and muscle, thereby increasing surgical time, patient trauma, blood loss, tissue damage, post-operative pain, recovery and healing periods, and treatment costs. Current methods to revise existing spinal implants also frequently entail the use of multiple and separate assemblies (e.g., various forms of screws, hook and or connectors linked by rods, wires, or plates), which can be inconvenient, reduce surgical accuracy; and further increase surgery time and costs. It would be desirable to reduce or eliminate these and other drawbacks of revising an existing implant by providing a revision implant having a minimal number of components and which may be installed in the spine of a patient percutaneously, improve placement in the spine of patient during surgery, and reduce or eliminate the need to significantly disrupt or remove the existing implant in order to achieve the desired revision.

The present invention satisfies the above-described needs and provides other benefits and advantages in a novel and nonobvious manner.

SUMMARY

The present invention relates generally to an instrument and system for percutaneously delivering and installing a percutaneous revision implant into a spinal region of a patient having an existing implant previously installed therein, and methods of using same. More particularly, the percutaneous delivery instrument of the present invention may be used to percutaneously deliver a revision implant to a surgical site in order to revise (e.g., extend) an existing implant, without significantly disrupting or removing the existing implant or its component parts. While the actual nature of the invention covered herein can only be determined with reference to the claims appended hereto, certain forms of the invention that are characteristic of the preferred embodiments disclosed herein are described briefly as follows.

In accordance with the present invention, a delivery instrument for use in percutaneous revision-type procedures to percutaneously deliver a spinal implant to a surgical site located in a spinal region of a patient having an existing implant installed therein is provided. Once implanted using the delivery instrument, the percutaneous spinal implant may be useful for revising an existing spinal construct by, for example, extending the existing implant to span additional portions of the spine of a patient. The delivery instrument generally comprises a translator and a shaft assembly comprising an inner shaft and an outer sleeve.

Also in accordance with the present invention, a spinal surgical system is provided. The spinal surgical system generally comprises the aforementioned delivery instrument, a percutaneous revision implant, an existing spinal implant, and a new bone fastener.

Further according to the present invention, methods of using the aforementioned delivery instrument and/or spinal surgical system to revise an existing spinal implant construct, without removing or significantly disrupting the existing implant and/or its hardware components, are also provided. In one embodiment, the method comprises the step of obtaining access to a post-operative spinal region of the patient in a minimally invasive manner, such as by providing one or more percutaneous access sites (e.g., stabs, punctures, micro-incisions) in the spinal region of a patient. The method further comprises the step of installing a new bone fastener in a portion of the spine adjacent the spinal region having the existing implant implanted therein through the one or more percutaneous access sites. The method further comprises the steps of employing the percutaneous delivery instrument of the invention to introduce and install a spinal implant into the surgical site through a percutaneous access site and engage portions of the revision implant with the existing implant and new bone fastener. The method may further comprise the step of installing a set screw to secure engagement between the percutaneous revision implant and the existing implant. In some embodiments, the method is performed entirely through one percutaneous access site. By engaging or locking notches, grooves, ribs or like features of the delivery instrument with notches, grooves, ribs or similar features of a spinal implant, the medical practitioner may deliver and install the revision implant in a precise manner during a percutaneous-type revision procedure. The method may comprise additional steps as discussed in more detail herein.

It is one object of the present invention to provide improved instruments and methods for percutaneously delivering a revision implant to a surgical site in the spinal region of a patient in order to revise an existing implant installed in the spine. Further objects, features, advantages, benefits, and aspects of the present invention will become apparent from the drawings and description contained herein.

BRIEF DESCRIPTION OF THE DRAWINGS

FIG. 2 is a perspective view of the inner shaft component of FIG. 1.

FIG. 3 is a perspective view of the outer sleeve component of FIG. 1.

DETAILED DESCRIPTION

Figure 1:
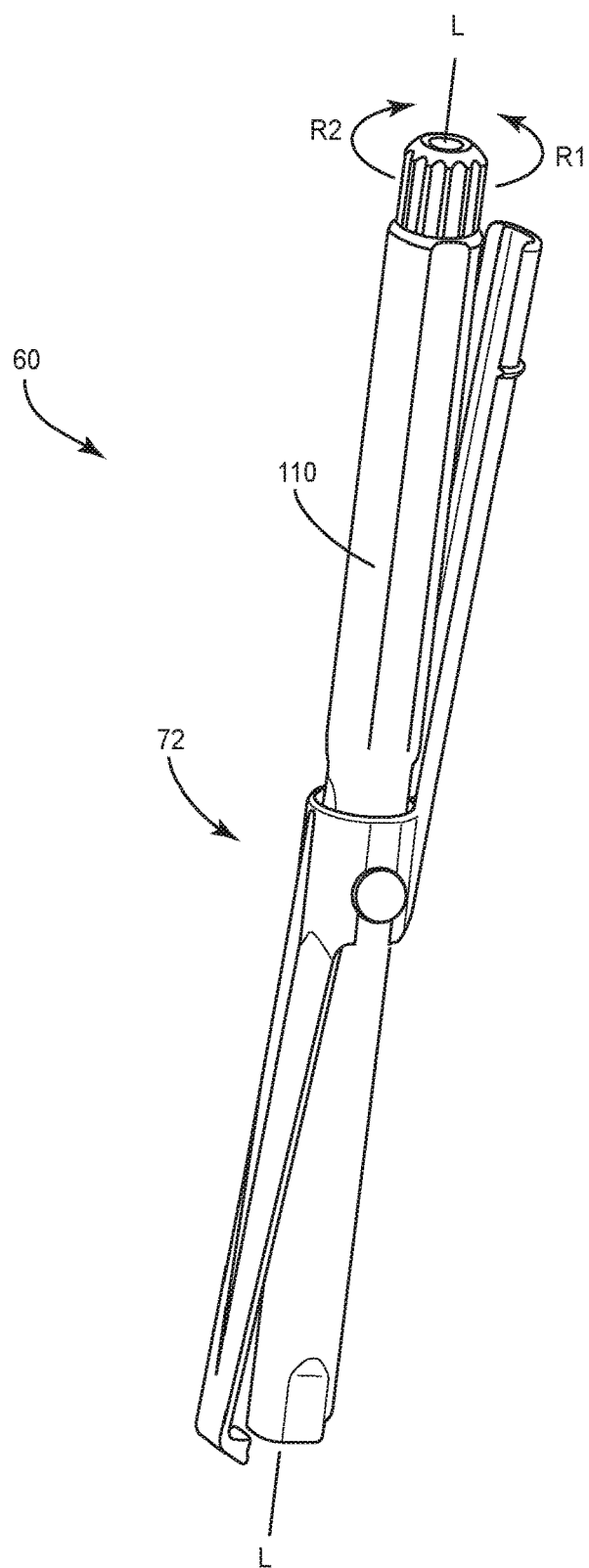
FIG. 1 is a perspective view of an embodiment of the delivery instrument in accordance with the principles of the present disclosure.

The exemplary embodiments of the invention and related methods of use disclosed are discussed in terms of medical devices for the treatment of musculoskeletal disorders and more particularly, in terms of a delivery instrument and spinal surgical system for percutaneously delivering a revision implant to a surgical site to treat the spine of patient having an existing spinal implant, and methods of using the same for treating a spine.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present embodiments may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, upward, downward, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The components of the invention can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide; polyetherimide, polyethylene, epoxy, bone material including autograft, allograft, xenograft or transgenic cortical and/or corticocancellous bone; and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity; elasticity, compliance, biomechanical performance, durability and radiolucency or imaging preference. The components of the invention, individually or collectively, may also be fabricated from a heterogeneous material such as a combination of two or more of the above-described materials. The components of the invention may be monolithically formed, integrally connected or include fastening elements and/or instruments, as described herein.

It is envisioned that the percutaneous delivery instrument of the invention will be employed, for example, with a minimally invasive procedure, including percutaneous techniques, mini-open and open surgical techniques, to deliver and introduce, deliver, and install an implant, such as, for example, a percutaneous revision implant, at a surgical site within a body of a patient, for example, a section of a spine. It is contemplated that the delivery instrument (and typical revision implant) and method may be employed with treatments using minimally invasive and percutaneous techniques.

For the purposes of promoting an understanding of the principles of the invention, reference will now be made to exemplary embodiments of the present disclosure, which are illustrated in the accompanying figures (FIGS. 1-16), and specific language will be used to describe the same. Alternate embodiments are also disclosed. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Referring now to FIG. 1, shown therein is an embodiment of delivery instrument 60 of the present invention. Delivery instrument 60 generally comprises a shaft assembly 110 comprising an inner shaft 61 and an outer sleeve 66, and a translator 72. Once assembled, the components of delivery instrument 60 extend along a longitudinal axis L. Delivery instrument 60 will be useful for delivering and installing a revision implant 10 into a surgical site located in a spinal region of a patient having an existing implant installed therein and adjacent spinal regions, thereby achieving revision of an existing implant 40 in a percutaneous revision-type procedure. The revision achieved in a minimally invasive manner may include, for example, extending existing implant 40 to span additional portions of the spine of a patient.

FIG. 2 illustrates an embodiment of inner shaft component 61 having a proximal end 62 and a distal end 63. Proximal end 62 generally comprises a knob 64 which may be provided with ribs, grooves, beveling, or other features designed to facilitate gripping, moving and manipulation of component 61 or delivery instrument 60, by the medical practitioner. Distal end 63 of inner shaft 61 comprises a threaded portion 65 useful for engaging a threaded opening in a spinal implant. All or portions of inner shaft 61 will typically comprise a cylindrical shape, however, inner shaft 61 may comprise along its length portions having varying diameter. In some embodiments, the diameter of knob 64 will be larger than the remainder of inner shaft 61. In some embodiments, the diameter of threaded portion 65 will be smaller than the remainder of inner shaft 61. It will further be understood that other configurations are within the scope of the invention, including but not limited to, configurations having square, rectangular, oval, elliptical, or polygonal cross-sections.

It will be further understood that inner shaft 61 is not limited to the exemplary embodiment of FIG. 2, and may be alternatively configured in other embodiments useful for the surgical applications described herein. For example, inner shaft 61 may comprise a set screw driver having a threaded set screw attached at distal end 63. In some embodiments, the set screw will be retained by inner shaft 61 in one position, and released from distal end 63 in another position.

Figure 11:
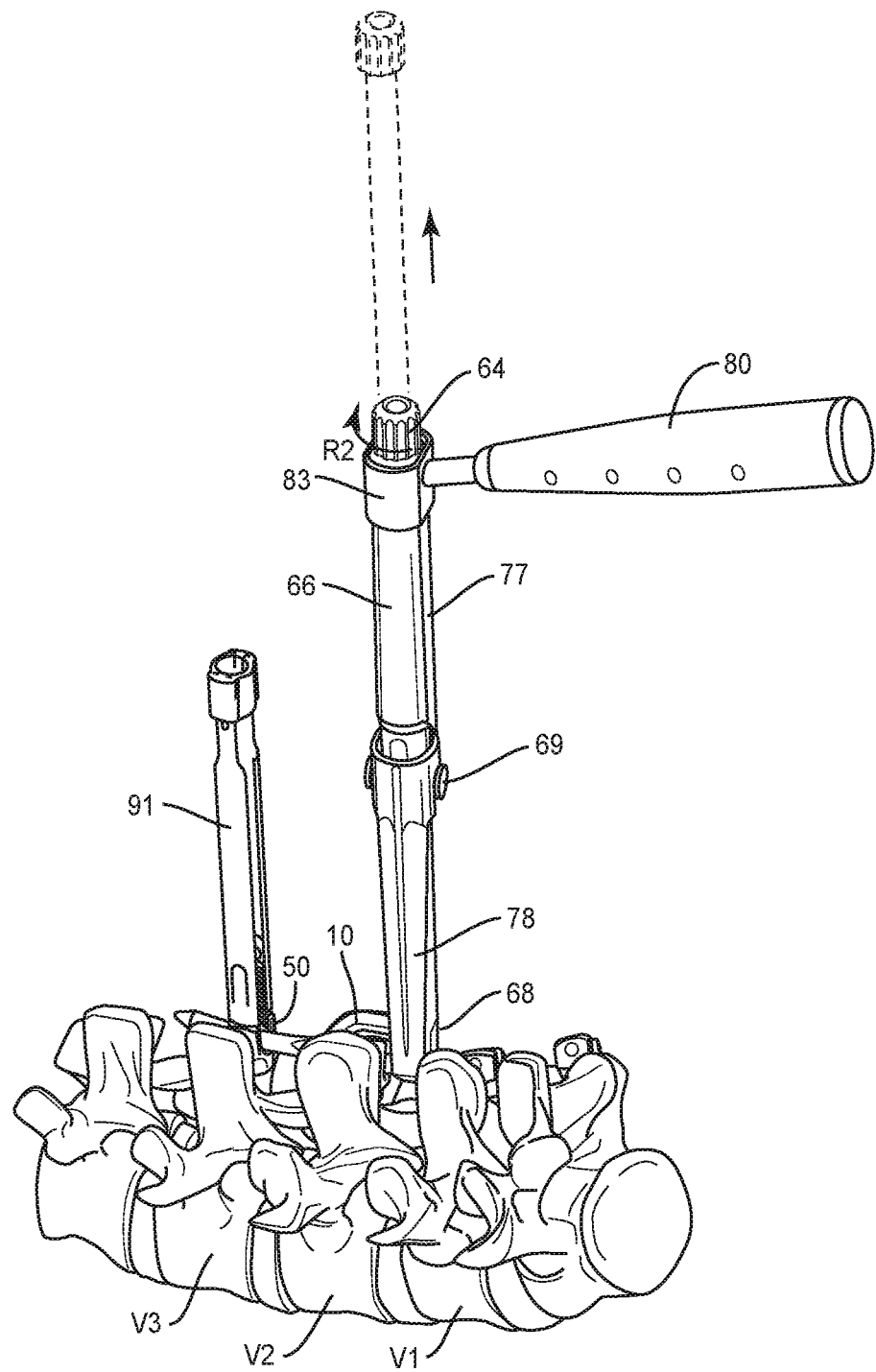
FIG. 11 is a perspective view of the components of FIG. 10 engaged by the counter torque of FIG. 6.

FIG. 3 illustrates an embodiment of outer sleeve 66 according to the present invention. Outer sleeve 66 comprises a member having a proximal end 67 and a distal end 68, and defines a hollow cavity 100 for disposing and positioning therein, various tools known in the art to be usefully employed in spinal surgical procedures, including but not limited to, shafts, drivers, screws, wires, hooks, rods, etc. In accordance with the invention, when delivery instrument 60 is assembled, inner shaft 61 may be disposed in all or a portion of hollow cavity 100 by inserting along longitudinal axis L. More particularly, the medical practitioner may move the inner shaft upwards or downwards in the hollow cavity by employing a sliding motion along longitudinal axis L, as shown in FIG. 11, as may be necessary during a surgical procedure to percutaneously deliver and install a spinal implant into a desired spinal region of a patient. Inner shaft 61 may also be rotated about longitudinal axis L in a first direction R1 or second direction R2 (i.e., clockwise or counter-clockwise) (as in FIG. 1) in order to advance or withdraw inner shaft 61, and particularly threaded portion 65, into or from (e.g., screw or unscrew) a suitable threaded opening in a spinal implant.

Figure 4:
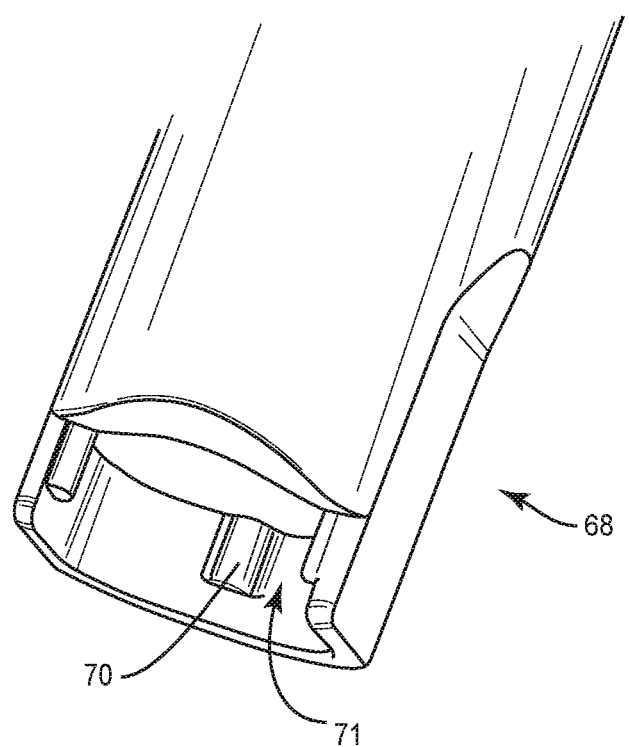
FIG. 4 is an enlarged perspective view of the distal end of the component in FIG. 3.

Outer sleeve 66 further comprises one or more hinge pins 69 for engaging and/or forming a locking connection with additional components of the invention, such as translator 72. In one embodiment and as illustrated in FIGS. 3 and 4, distal end 68 comprises grooves 70 for engaging and/or locking onto revision implant 10 having similar grooves, notches, ribs, or similar features. It is contemplated, however, that distal end 68 may also be configured to comprise other ribs, hooks, notches, or the like, suitable for engaging and/or locking onto a spinal implant configured for percutaneous-type revision procedures. Distal end 68 further comprises a portion shortened in longitudinal length to define an inlet 71. Generally, inlet 71 provides space for translator 72 to clamp onto a portion of an existing spinal implant, thereby ensuring that the revision implant is positioned as desired (e.g., on the existing rod 23). Outer sleeve 66 may be generally cylindrical in shape, though diameter may vary along portions of its length. In one embodiment, the diameter of a portion of proximal end 67, typically above hinge pins 69, transitions to a smaller diameter towards distal end 68. In some embodiments proximal end portion 67 may be non-cylindrical and comprise one or more flattened edges such that a cross-section of the proximal end 67 comprises a polygonal configuration. Outer sleeve 66 may further be provided with ribbing, beveling, indentations, or other patterns which facilitate gripping, moving and manipulating of delivery instrument 60 by the medical practitioner and/or to provide traction against portions of translator 72. Distal end 68 may be provided with beveling or one or more flattened edges.

Shaft assembly 110 comprises the aforementioned inner shaft 61 and outer sleeve 66. As described herein, the components of shaft assembly 110 are configured to engage a revision implant and introduce it to a surgical site having an existing implant installed therein. In one embodiment, shaft assembly 110 may be useful for engaging revision implant 10 with the existing implant. Shaft assembly 110 may bring revision implant 10 into full or partial engagement (i.e., not fully seated) with existing rod 23.

Figure 5:
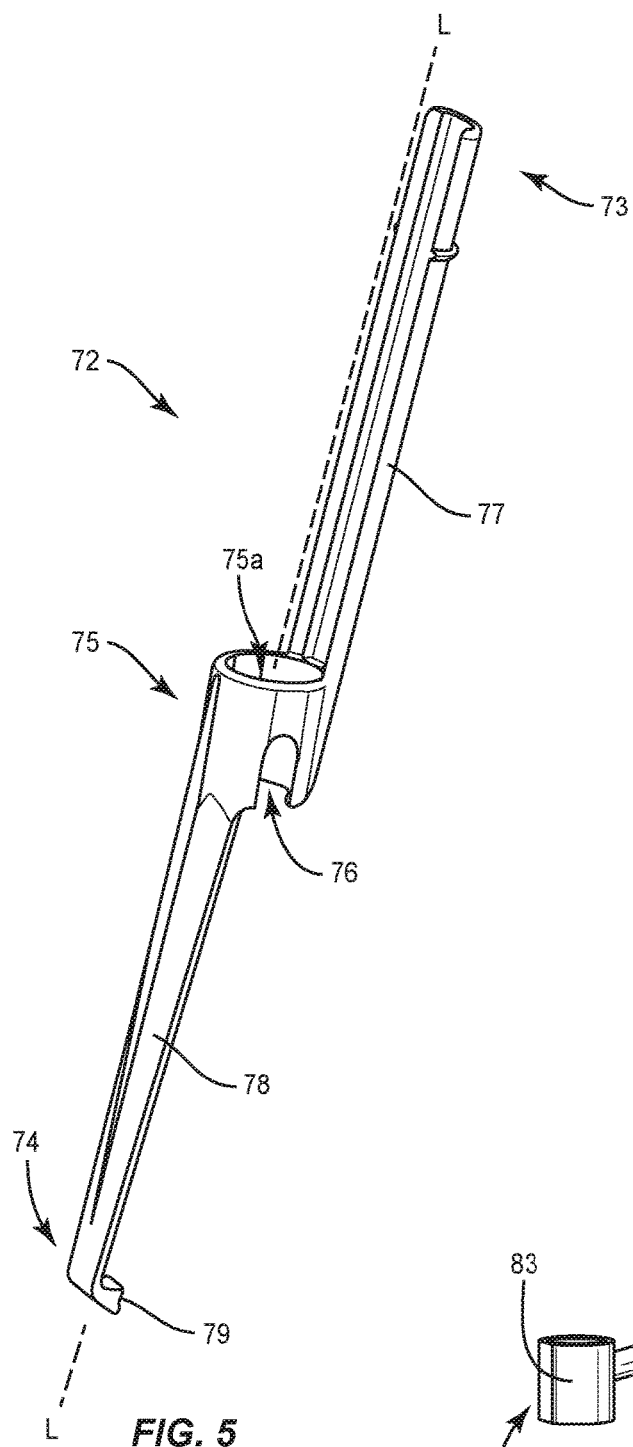
FIG. 5 is a perspective view of the translator component of FIG. 1.

Delivery instrument 60 further comprises a translator component 72 having a proximal end 73 and a distal end 74, as illustrated in FIG. 5. Translator 72 generally comprises intermediate piece 75, a first extension piece 77 extending parallel to longitudinal axis L from intermediate piece 75 to proximal end 73, and a second extension piece 78 extending parallel to longitudinal axis L from intermediate piece 75 to distal end 74. Translator 72 is sized and configured to slide over outer sleeve 66.

Intermediate piece 75 defines cavity 75a. Typically, intermediate piece 75 comprises a cylindrical shape for surrounding a circumference of outer sleeve 66. However, it will be understood that intermediate piece 75 may take other configurations provided that cavity 75a is large enough to allow translator 72 to slide over and engage outer sleeve 66. Intermediate piece 75 further comprises one or more apertures 76 to engage hinge pins 69. In some embodiments, the one or more apertures 76 may be U-shaped.

First extension piece 77 and second extension piece 78 are each configured to engage a portion of the circumference of outer sleeve 66 when translator 72 is positioned over outer sleeve 66. Typically, the configuration of first extension piece 77 is such that a cross-section comprises a semi-circle or arch. Second extension piece 78 may be tapered. However, it will be understood that first and second extension pieces 77 and 78 may be otherwise configured. Proximate or at distal end 74, second extension piece 79 further comprises a clamp 79 for engaging a portion of an existing implant 40, such as existing rod 23.

Figure 9:
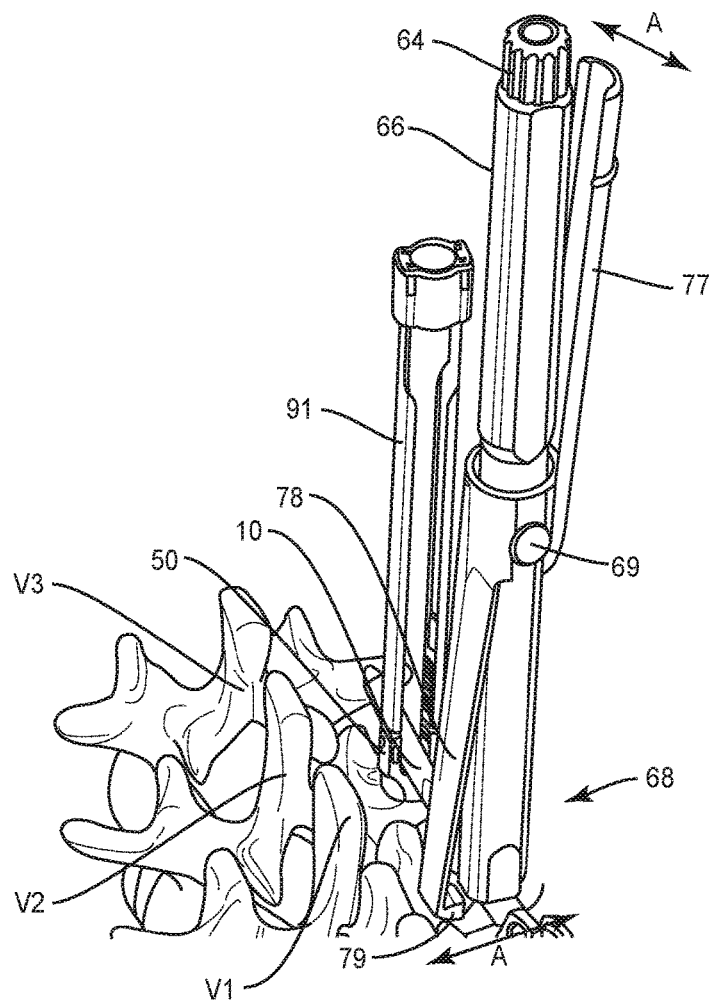
FIG. 9 is a perspective view of an embodiment of the spinal surgical system with the component of FIG. 5 in first position.
Figure 10:
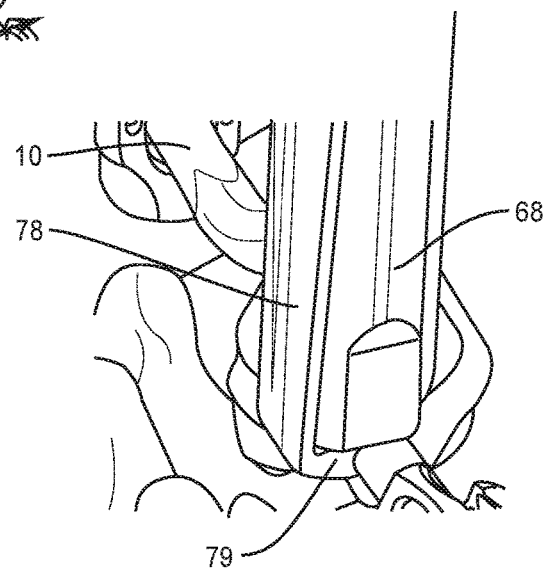
FIG. 10 is a perspective view of an embodiment of the spinal surgical system with the component of FIG. 5 in second position.

In one embodiment, illustrated in FIG. 5, first extension piece 77 and second extension piece 78 are offset from longitudinal axis L and each other. The engagement between hinge pins 69 and apertures 76 permits movement of first and second extension pieces 77 and 78 into and out of contact with outer sleeve 66. In particular, translator 72 may be moved (e.g., squeezed) such that first and second extension pieces 77 and 78 move in tandem along a path A, which may be arcuate, from a first position out of contact with outer sleeve 66 to a second position in contact with a circumference of outer sleeve 66, as illustrated in FIGS. 9 and 10.

In the first position, at least a portion of first and second extension pieces 77 and 78 is out of contact with outer sleeve 66. In some embodiments, revision implant 10 (engaged with shaft assembly 110) may be partially seated (i.e., not fully seated) on existing rod 23. The second position typically achieved by squeezing translator 72, brings first and second extension pieces 77 and 78 into engagement with a circumference of outer sleeve 66. Clamp 79 may engage a portion of an existing implant 40 such as existing rod 23. Movement along path A from the first position to the second position will be useful in permitting a medical practitioner to engage and release a spinal implant and/or existing implant during percutaneous introduction and installation into a surgical site, and to position a revision implant on the existing implant as desired. Alternate paths of movement suitable to facilitate similar engagement and release of a spinal implant and/or existing implant during minimally invasive surgical procedures are also within the scope of the invention disclosed herein. More particularly, movement along path A from the first position to the second position will be useful for fully seating revision implant 10 on existing rod 23. The force of translator 72 may move revision implant 10 into full engagement with existing implant 40.

According to the present invention, a spinal surgical system is also provided. The spinal surgical system generally comprises the aforementioned delivery instrument 60, a revision implant 10, an existing implant 40, and a new bone fastener 50. Revision implant 10 may comprise any spinal implant for percutaneously revising an existing spinal construct which is configured to engage with delivery instrument 60.

Existing implant 40 (FIG. 14) is understood to have been installed in one or more prior surgical procedures. Existing implant 40 generally comprises one or more existing bone fasteners 20 installed in one or more vertebra of the spine. Bone fasteners 20 comprise a shank 21 installed in the spine and having a receiver head 22 attached thereto. Existing implant 40 further comprises at least one existing rod 23, a portion of which is engaged by receiver head 22. In one embodiment, existing bone fasteners 20 are installed in a first vertebra V1 and a second vertebra V2. Set screws 24 may also be included to secure existing rod 23 in place. Existing implant 40 may further comprise additional components known in the field, including but not limited to, screws, plates, hooks, ties, and wires. While embodiments of existing implant 40 spanning two vertebras are illustrated, it is understood that existing implant 40 may span additional portions of the spine.

The spinal implant system of the present invention further comprises one or more new bone fasteners 50 for engaging percutaneous rod 17. In one embodiment, one or more new bone fasteners 50 are newly installed in at least one vertebra V3 adjacent the one or more vertebra V1, V2 having an existing implant installed therein. The one or more new bone fasteners 50, may be the same or similar to the above-described one or more bone fasteners 20 of existing implant 40, but may also be other bone fasteners known in the field suitable to engage a spinal rod. The spinal implant system may further comprise a component for securing a spinal rod in bone fasteners 50, such as set screw. It is understood that other means for securing such engagement, including but not limited to screws, hooks, ties or wires, are within the scope of the invention.

In the spinal implant system, revision implant 10 may be oriented in various manners relative to existing implant 40, including in any manner that may be necessary to accommodate the unique dimensions of the various spinal structures of individual patients. In particular, revision implant 10 may be oriented to accommodate the natural curvature of the spine. In one embodiment, revision implant 10 is disposed to extend along an axial plane, such as for example, a sagittal plane of a body of a patient. Revision implant 10, however, may be disposed to extend along a coronal, sagital or transverse plane of the body and geometric variations thereof.

A method of using delivery instrument 60 in accordance with the invention is now described with reference to FIGS. 7-13. The method involves employing the percutaneous delivery instrument of the invention to deliver and install a percutaneous revision implant into a spinal region having an existing implant installed therein and an adjacent spinal region in order to revise an existing spinal implant, without removing or significantly disrupting the existing implant and/or its hardware components.

The method of the present invention may comprise the step of obtaining access to a post-operative spinal region of the patient having the existing implant installed therein and adjacent spinal regions as required for the particular application. In accordance with the present invention, access is obtained to a surgical site in any appropriate manner, such as through incision and retraction of tissues, in a minimally invasive manner. Typically one or more percutaneous access sites (e.g., stabs, punctures, micro-incisions, sleeves, protected passageways) will be provided in the spinal region of a patient. The one or more incisions or punctures made in the body of the patient create one or a plurality of percutaneous surgical pathways and/or openings for implantation of components of the surgical system. For example a percutaneous stab or incision creates a surgical pathway for delivering revision implant 10 and/or new bone fasteners 50 to the surgical site. A preparation instrument (not shown) can be employed to prepare tissue surfaces of vertebra (V1, V2, V3), as well as for aspiration and irrigation of a surgical region according to the requirements of a particular surgical application.

Once a percutaneous surgical pathway and access site to the surgical site is obtained, the particular surgical procedure is performed for treating the spinal disorder, and for extending or other revising the existing implant. The components of the spinal system are then employed to augment the surgical treatment. One or all of the components of the surgical system may be completely or partially revised, removed or replaced during or after the surgical procedure.

The method may further comprise the step of installing one or more new bone fasteners 50 in a portion of the spine adjacent the spinal region having existing implant 40 implanted therein through the one or more percutaneous access sites. One or more new bone fasteners 50 may be installed in at least one vertebra adjacent the one or more vertebra V1, V2 having an existing implant installed therein, such as adjacent vertebra V3. In another embodiment, the method further comprises installing bone fastener 50 by accessing the adjacent vertebra V3 through the same percutaneous access site and/or surgical pathway used to introduce revision implant 10 to the surgical site. It is understood that bone fastener 50 may be installed at any point during the procedure which allows for the desired placement of revision implant 10 to treat the spine of the patient.

The method further comprises the step of engaging and/or locking shaft assembly 110 comprising inner shaft 61 and outer sleeve 66 with a suitably configured percutaneous spinal implant. The step may entail lining up grooves 70 or similar features of outer sleeve 66 (e.g., notches, ribs, hooks) with features of a spinal implant for engaging and/or locking onto a percutaneous delivery instrument. The step may further comprise screwing the threaded portion 65 of percutaneous delivery instrument 60 into a threaded opening of spinal implant. The step may be achieved by moving knob 64 in a first direction R1 about longitudinal axis L to advance threaded portion 65 into the threaded opening in accordance with the particular application. Additional instruments known in the art, including but not limited to extenders and collars, such as extender 91 may be employed by the user to facilitate this and other steps of the method of the invention.

Figure 15:
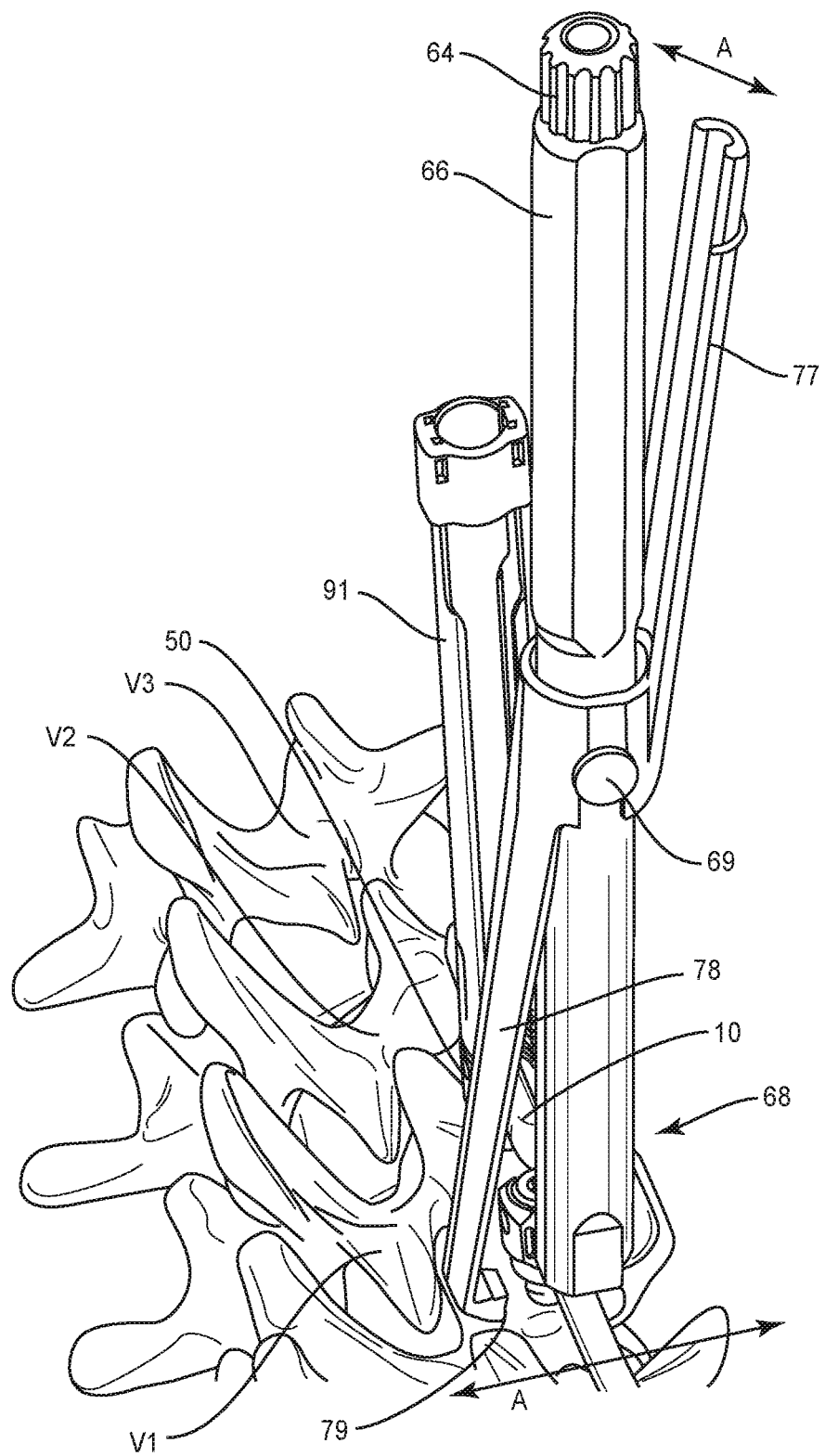
FIG. 15 is a perspective view of an embodiment of the delivery instrument with the revision implant attached thereto partially seated on an existing rod.
Figure 16:
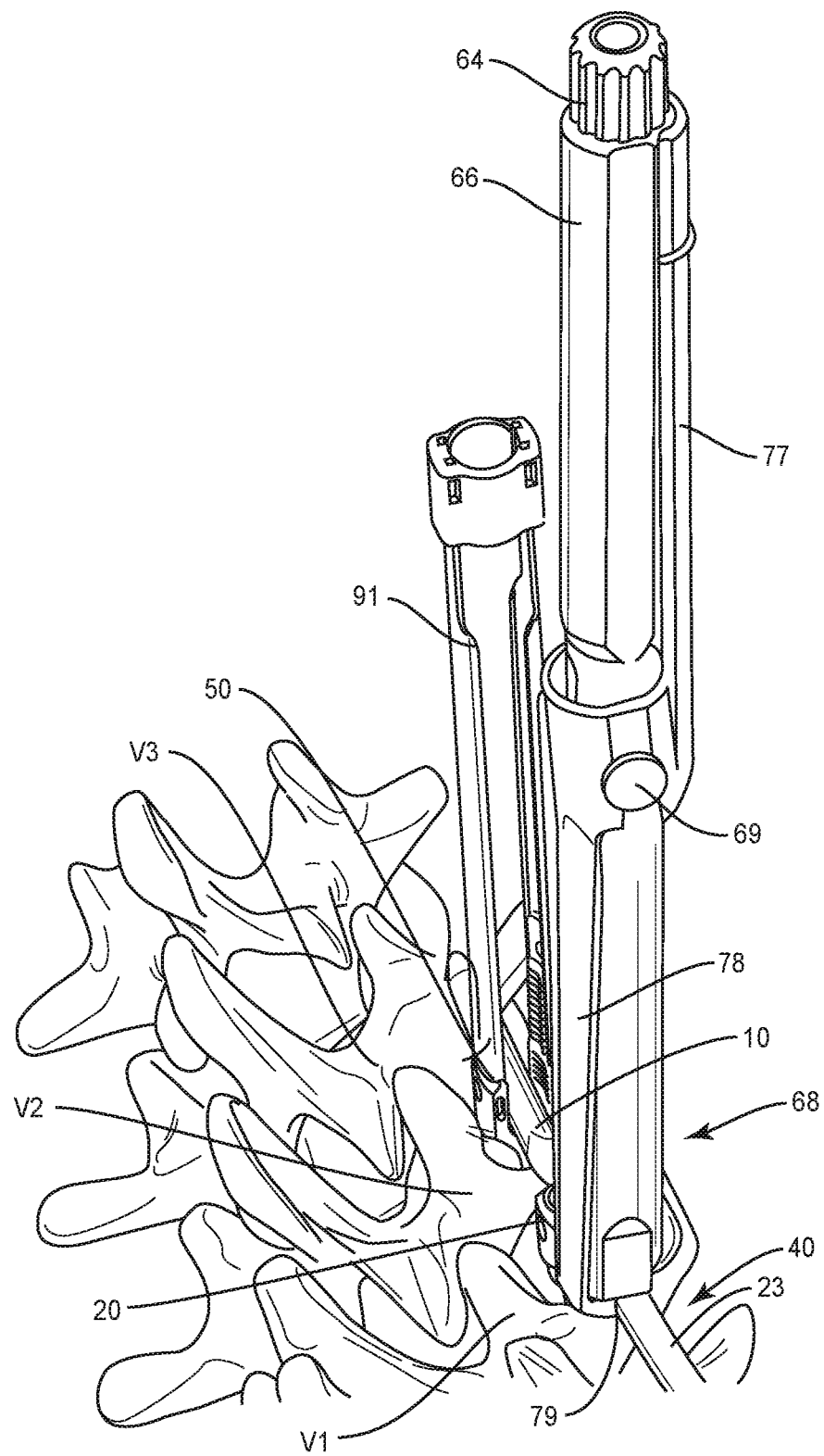
FIG. 16 is a perspective view of an embodiment of the delivery instrument with the revision implant attached thereto fully seated on the existing rod.

The method further comprises the step of introducing (i.e., delivering) percutaneous revision implant 10 to the surgical site by employing shaft assembly 110. The method further comprises delivering and installing revision implant 10 by employing percutaneous delivery instrument 60. Typically, the step comprises engaging the revision implant 10 with existing rod 23 and through new bone fastener 50. The method further comprises sliding translator 72 over the top of and onto outer sleeve 66. The user may move (e.g., squeeze) translator 72 such that first and second extension pieces 77 and 78 move in tandem from a first position to a second position along path A (shown in FIG. 9) thereby by bringing translator 72 in contact with outer sleeve 66, and bringing revision implant 10 into full engagement with existing rod 23. Clamp 79 contacts existing rod 23 to ensure revision implant 10 is positioned as desired on existing rod 23, as illustrated in FIGS. 9, 15 and 16.

Figure 6:
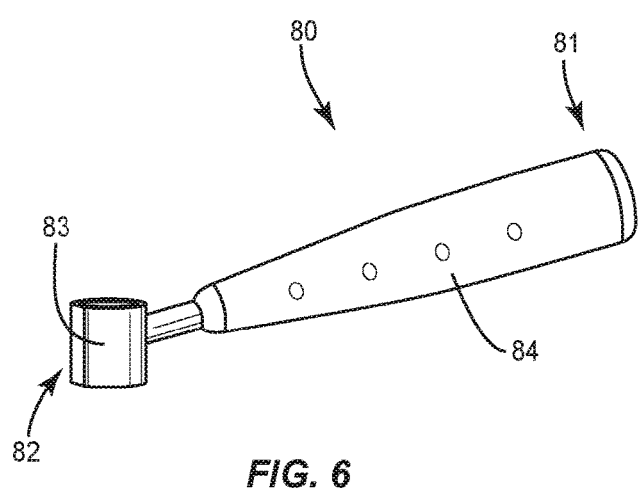
FIG. 6 is a perspective view of an embodiment of a counter torque component in accordance with the principles of the present disclosure.
Figure 7:
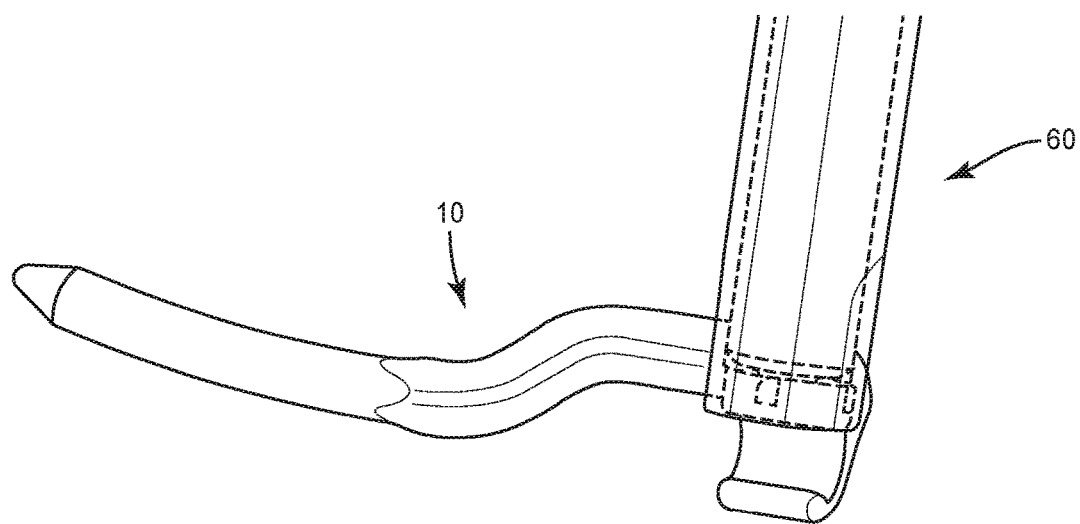
FIG. 7 is an enlarged perspective view of the delivery instrument of FIG. 1 attached to a spinal implant.
Figure 8:
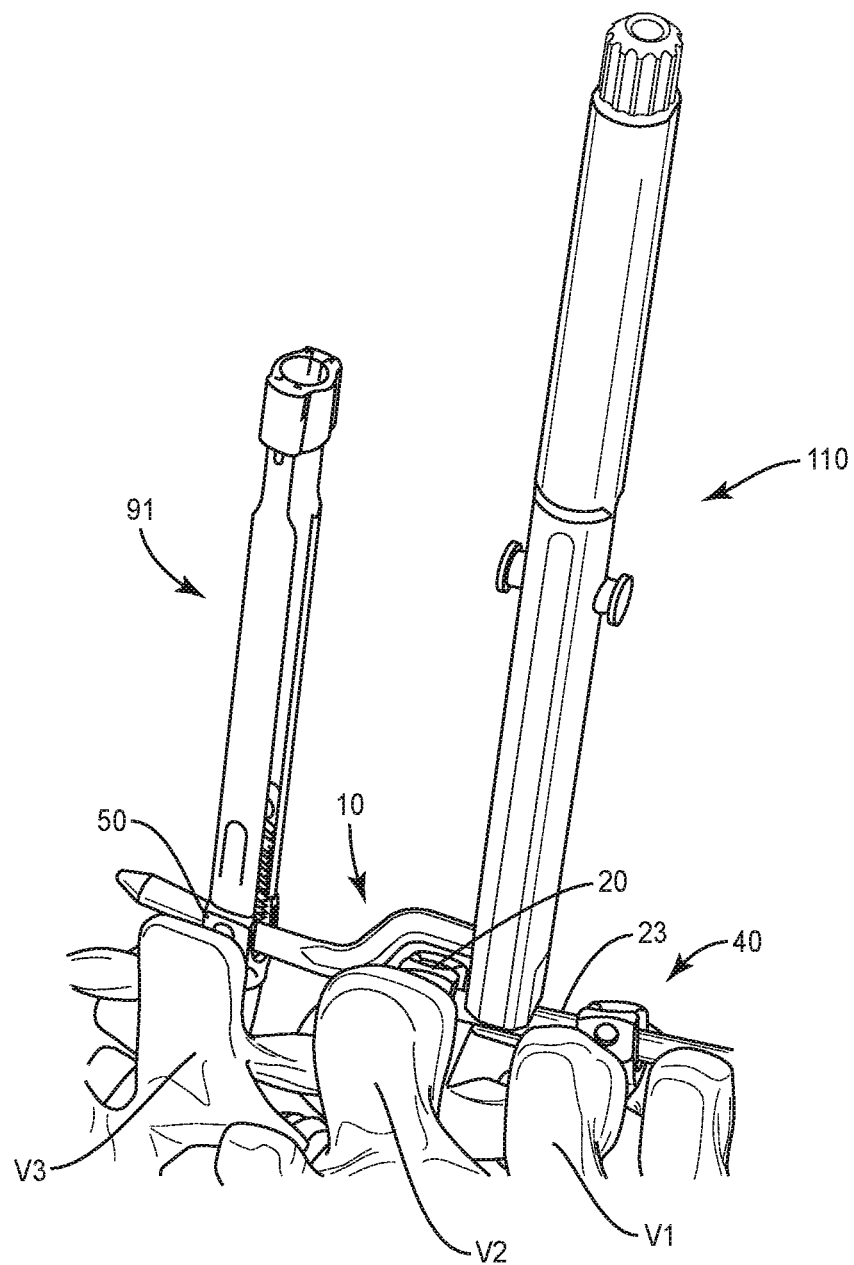
FIG. 8 is a perspective view of an embodiment of the spinal surgical system according to the invention attached to the spine.

The method may further comprise the step of positioning a counter torque 80 over proximal end 67 of the outer sleeve 66, typically adjacent to knob 64, to secure the percutaneous delivery instrument in position. Referring to FIG. 6, in one embodiment, counter torque 80 includes a proximal end 81 and a distal end 82. Counter torque 80 generally comprises a collar 83 for sliding onto and/or positioning the counter torque over proximal end 67, and a handle 84. Handle 84 may be bulbous or comprise other configurations suitable to facilitate application of pressure or torque by the user.

The method according to the invention may further comprise removing inner shaft 61 from hollow cavity 100 to allow for placement of set screws through the hollow cavity. Inner shaft 61 may be removed by moving (e.g., twisting) knob 64 in a second direction R1 about longitudinal axis L to withdraw threaded portion 65 from the threaded opening, and further by sliding inner shaft 61 along longitudinal axis L in a proximal direction. An embodiment of this step is illustrated in FIG. 11.

Figure 12:
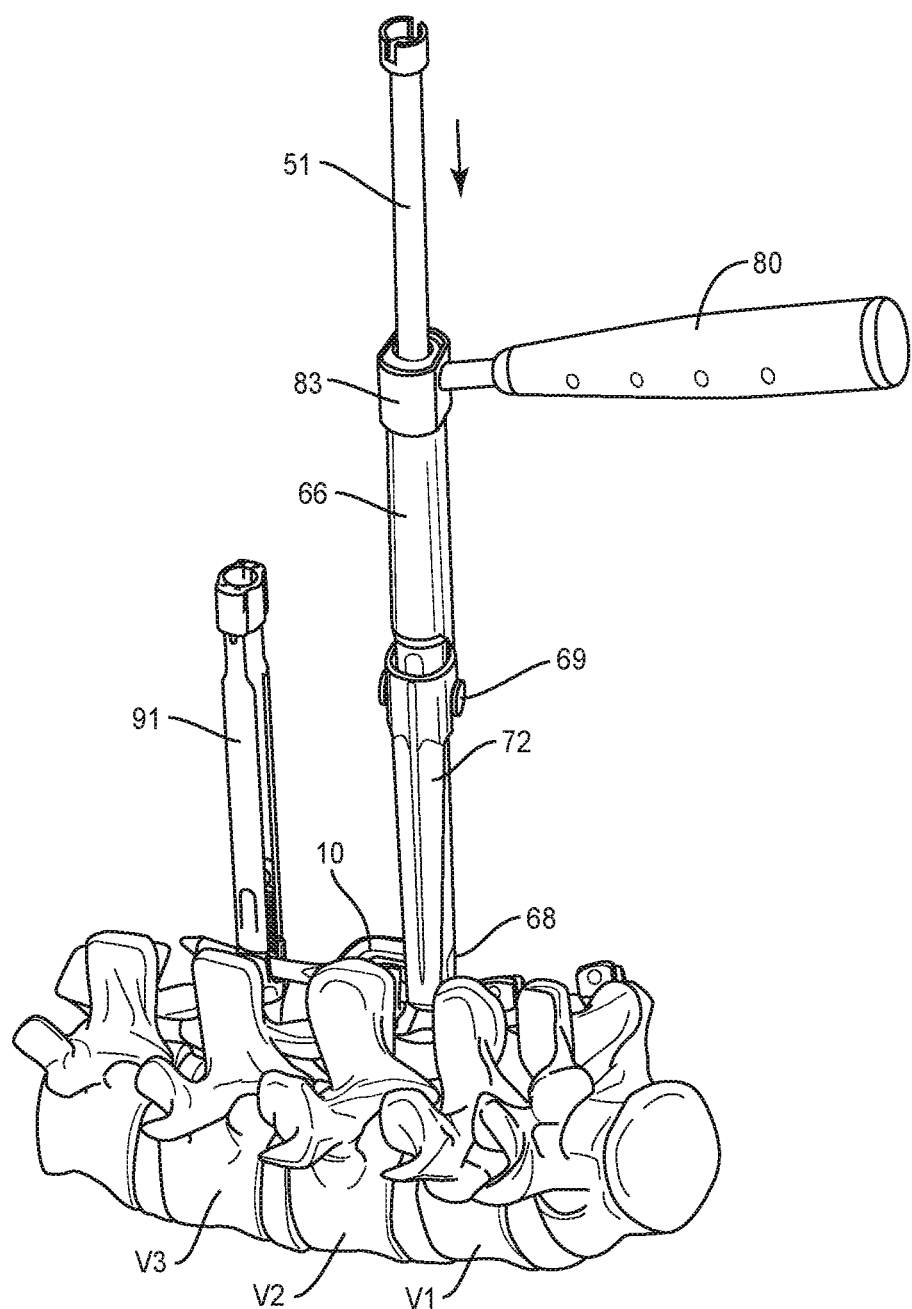
FIG. 12 is a perspective view of the components of FIG. 10 with a set screw disposed therein.
Figure 13:
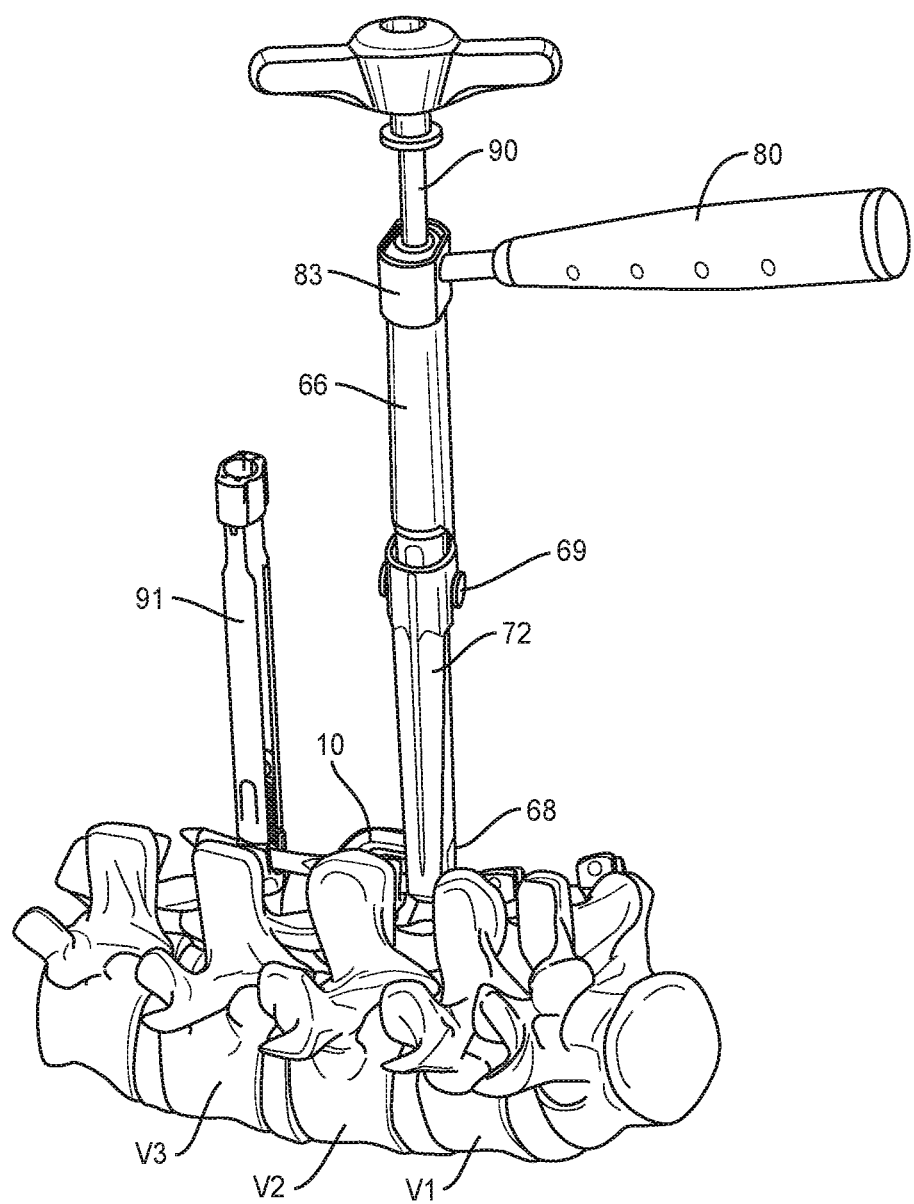
FIG. 13 is a perspective view of the components of FIG. 10 with a break-off driver disposed therein and engaged by the counter torque of FIG. 6.
Figure 14:
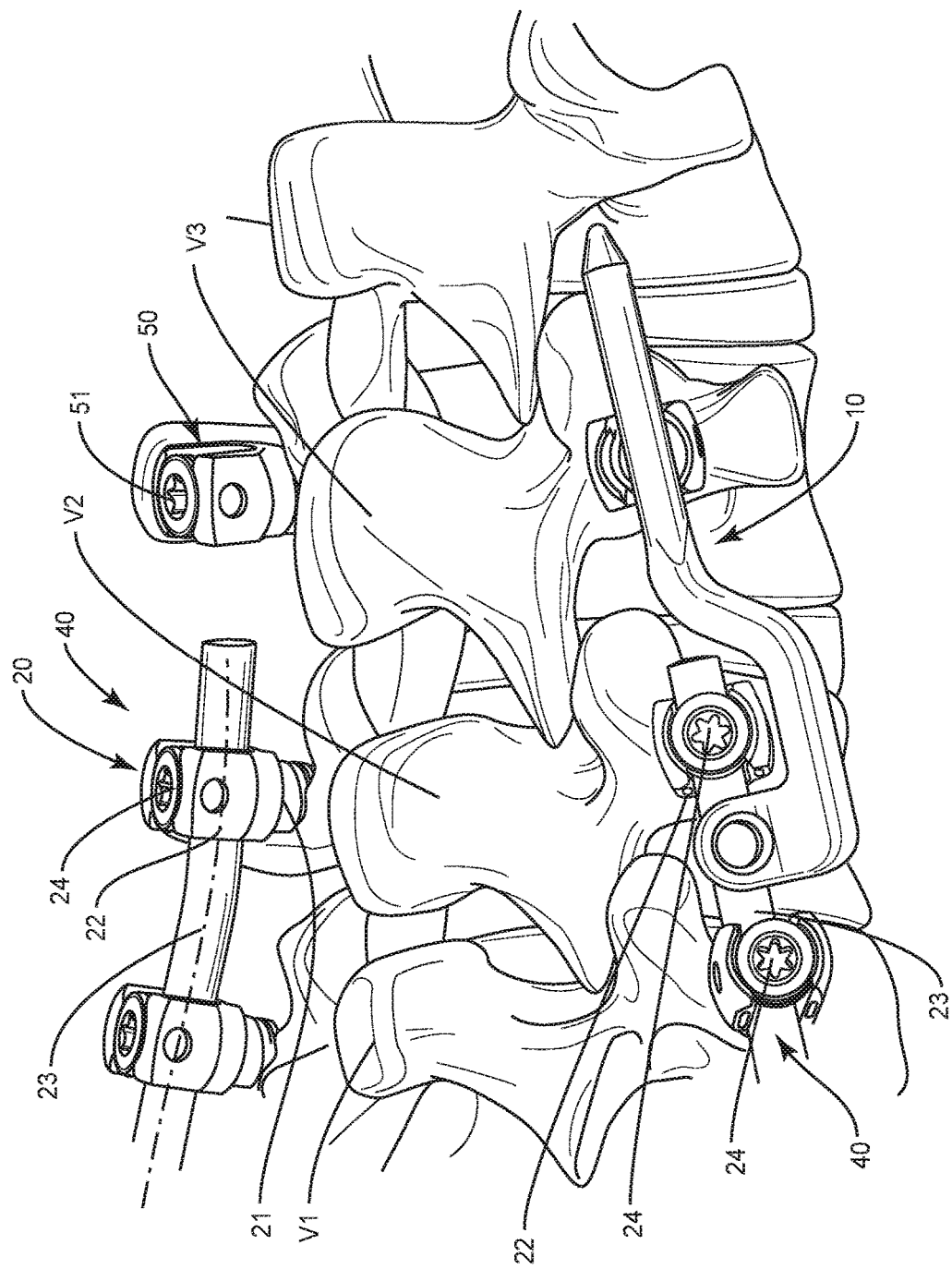
FIG. 14 is a perspective view of an embodiment of the existing implant.

Referring now to FIGS. 12 and 13, the method may further comprise installing a set screw through hollow cavity 100 of outer sleeve 66. The set screw 51 may be screwed into the threaded opening of revision implant 10. Such step may entail advancing set screw 51 along longitudinal axis L towards distal end 68 of outer sleeve 66. The method may further comprise inserting additional instrumentation known in the art into hollow cavity 100 as required to install revision implant 10 to revise the existing implant 40, for example, a break-off driver 90.

Where inner shaft 61 comprises a set screw driver having a set screw attached at distal end 63 and configured to selectively retain and release the set screw, the method may alternatively comprise the steps of engaging the set screw retained at distal end 63 with a threaded opening of revision implant 10 while inner shaft 61 is inserted in hollow cavity 100. In this step, inner shaft 61 typically will require removal from hollow cavity 100 during introduction, delivery and installation of revision implant 10.

The methods described herein will be useful for percutaneously delivering and installing a spinal implant to a spinal region of a patient having an existing implant installed therein and an adjacent spinal region, without significantly disrupting or removing the existing implant and its component parts, and in a manner with improved precision. In some embodiments, the method is performed entirely through one percutaneous access site to the spinal region of the patient.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

The invention claimed is:

1. A delivery instrument for percutaneously delivering a revision implant to a surgical site in a spine of a patient having an existing implant installed therein, the delivery instrument comprising:
    a shaft assembly comprising:
        an inner shaft having an outer surface and proximal and distal ends, said proximal end comprising a knob and said distal end comprising a threaded portion for engaging a portion of the percutaneous revision implant, and
        a monolithic outer sleeve having proximal and distal ends, said outer sleeve comprising an inner surface defining a hollow cavity, said inner shaft being positioned in said hollow cavity such that said outer surface is engageable with said inner surface, said outer sleeve having at least one hinge pin along the length of the outer sleeve, said distal end of said outer sleeve being configured to engage the percutaneous revision implant; and
    a translator comprising an intermediate piece and first and second extension pieces, said intermediate piece comprising a cylindrical wall defining a cavity configured for disposal of said shaft assembly, said cylindrical wall having at least one aperture for engaging the at least one hinge pin,
    wherein the delivery instrument extends along a longitudinal axis.

2. The delivery instrument of claim 1, wherein a diameter of the inner shaft distal end is smaller than a diameter of the inner shaft proximal end.

3. The delivery instrument of claim 1, wherein the knob comprises ribs.

4. The delivery instrument of claim 1, wherein the distal end of the outer sleeve comprises grooves, notches, ribs, or hooks, or a combination thereof for engaging a revision implant.

5. The delivery instrument of claim 1, wherein the distal end of the outer sleeve comprises a clamp for engaging an existing rod of the existing implant.

6. The delivery instrument of claim 1, wherein the inner shaft is rotatable about the longitudinal axis.

7. The delivery instrument of claim 1, wherein the inner shaft is disposable in the hollow cavity by movement in first longitudinal direction and removable from the hollow cavity by movement in a second longitudinal direction.

8. The delivery instrument of claim 1, wherein the first and second extension pieces are movable from a first position to a second position along an arcuate path.

9. The delivery instrument of claim 8, wherein first and second extension pieces move in tandem when moved from the first position to the second position.

10. The delivery instrument of claim 1, wherein the inner shaft comprises a set screw driver with a threaded set screw releasably attached to its distal end.

11. The delivery instrument of claim 1, wherein said at least one hinge pin extends from an outer surface of said outer sleeve, said outer surface being free of threads.

12. The delivery instrument of claim 1, wherein said first extension extends from a proximal end of said cylindrical wall and said second extension extends from a distal end of said cylindrical wall.

13. The delivery instrument of claim 1, wherein said extensions extend parallel to said longitudinal axis, said first extension being offset from said second extension.

14. A delivery instrument comprising:
    a monolithic outer sleeve comprising an inner surface defining a passageway, the outer sleeve having a pair of hinge pins extending outwardly from an outer surface of the outer sleeve;
    an inner shaft disposed in the passageway such that an outer surface of the inner shaft is engageable with the inner surface, a distal end of the inner shaft comprising a threaded portion; and
    a translator comprising a cylindrical wall defining a cavity, the outer sleeve being disposed in the cavity, the translator comprising first and second extension pieces extending from the cylindrical wall, the cylindrical wall having a pair of apertures, the hinge pins each being disposed in one of the apertures such that the translator is pivotable relative to the outer sleeve about the hinge pins.

15. The delivery instrument of claim 14, wherein the passageway defines a longitudinal axis, the translator being movable relative to the outer sleeve between a first position in which the extension pieces extend at a non-parallel angle relative to the longitudinal axis and a second position in which the extension pieces extend parallel to the longitudinal axis.

16. The delivery instrument of claim 15, wherein the extension pieces extend parallel to one another when the translator is in the first position and the second position.

17. The delivery instrument of claim 15, wherein the outer sleeve includes a wall defining the passageway, a distal end of the outer sleeve comprising an inlet extending through a thickness of the wall of the outer sleeve, the second extension piece comprising a flange, the flange being spaced apart from the inlet when the translator is in the first position, the flange being positioned in the inlet when the translator is in the second position.

18. The delivery instrument of claim 14, wherein the outer surface is free of threads.

19. The delivery instrument of claim 14, wherein the passageway has a circular cross-sectional configuration.

20. A delivery instrument comprising:
a monolithic outer sleeve comprising an outer surface and an opposite inner surface defining a passageway, the passageway extending along a longitudinal axis, the outer sleeve having a pair of hinge pins extending outwardly from the outer surface;
a monolithic inner shaft disposed in the passageway such that an outer surface of the inner shaft is engageable with the inner surface, a distal end of the inner shaft comprising a threaded portion; and
a translator comprising a cylindrical wall defining a cavity having a circular cross-sectional configuration, the outer sleeve being disposed in the cavity, the translator comprising a first extension piece extending from a proximal end of the cylindrical wall and a second extension piece extending from a distal end of the cylindrical wall, the first extension piece extending parallel to the second extension piece, the cylindrical wall having a pair of apertures, the hinge pins each being disposed in one of the apertures such that the translator is pivotable relative to the outer sleeve about the hinge pins,
wherein the translator is movable relative to the outer sleeve between a first position in which the extension pieces extend at a non-parallel angle relative to the longitudinal axis and a second position in which the extension pieces extend parallel to the longitudinal axis.

* * * * *